US006723861B2

(12) United States Patent
Balthasart

(10) Patent No.: US 6,723,861 B2
(45) Date of Patent: Apr. 20, 2004

(54) METHOD FOR PRODUCING OXIRANE

(75) Inventor: Dominique Balthasart, Brussels (BE)

(73) Assignee: Solvay (Societe Anonyme), Brussels (BE)

( * ) Notice: Subject to any disclaimer, the term of this patent is extended or adjusted under 35 U.S.C. 154(b) by 0 days.

(21) Appl. No.: 10/297,927

(22) PCT Filed: Jun. 26, 2001

(86) PCT No.: PCT/EP01/07271
§ 371 (c)(1),
(2), (4) Date: Dec. 19, 2002

(87) PCT Pub. No.: WO02/00635
PCT Pub. Date: Jan. 3, 2002

(65) Prior Publication Data
US 2003/0187285 A1 Oct. 2, 2003

(30) Foreign Application Priority Data
Jun. 28, 2000 (FR) ............................................. 00 08354

(51) Int. Cl.[7] ...................... C07D 301/12; C07D 301/19
(52) U.S. Cl. ....................................... 549/531; 549/529
(58) Field of Search .................................. 549/531, 529

(56) References Cited

U.S. PATENT DOCUMENTS

| 5,849,937 A | 12/1998 | Jubin, Jr. et al. ............ 549/529 |
| 6,479,680 B1 | 11/2002 | Bassler et al. .............. 549/529 |

FOREIGN PATENT DOCUMENTS

| WO | 99/24164 | 5/1999 |
| WO | 99/28029 | 6/1999 |
| WO | 99 32472 | 7/1999 |
| WO | 99/48882 | 9/1999 |
| WO | 99/48883 | 9/1999 |
| WO | 00/31057 | 6/2000 |

*Primary Examiner*—Ba K. Trinh
(74) *Attorney, Agent, or Firm*—Oblon, Spivak, McClelland, Maier & Neustadt, P.C.

(57) ABSTRACT

Process for manufacturing oxirane by reaction of an olefin with a peroxide compound in the presence of a catalyst and a solvent in at least two reactors arranged in series, each of which contains a portion of the catalyst, according to which two epoxidation reactions are carried out in series including intermediate distillation, to minimize the formation of by-products.

12 Claims, 1 Drawing Sheet

METHOD FOR PRODUCING OXIRANE

Figure 1:
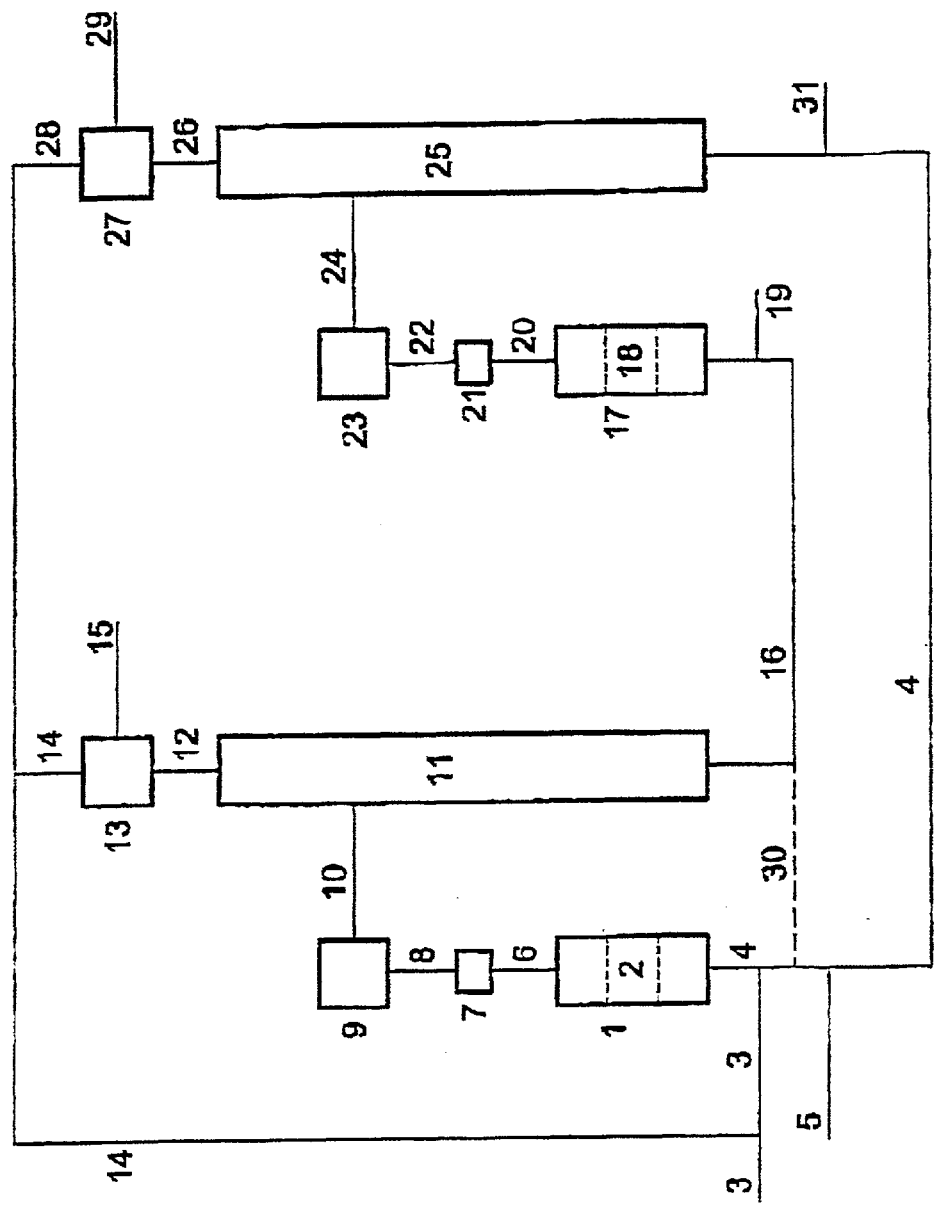

The present invention relates to a process for manufacturing oxirane by reaction between an olefin and a peroxide compound in the presence of a catalyst and a solvent. In particular, the invention relates to the manufacture of propylene oxide (or epichlorohydrin) by epoxidation of propylene (or allyl chloride) using hydrogen peroxide in the presence of a catalyst containing TS-1.

It is known practice to manufacture propylene oxide by reaction between propylene and a peroxide compound in the presence of TS-1. For example, in U.S. Pat. No. 5,849,937, such a process is performed in several reactors arranged in series.

The Applicant has found that this process has the drawback of resulting in the formation of by-products, for example when an aqueous hydrogen peroxide solution is used as peroxide compound and methanol is used as solvent in this known process. Specifically, when propylene oxide is manufactured under these conditions, by-products are formed by reaction between the propylene oxide and water or methanol, and in particular propylene glycol and methoxypropanols of formulae $CH_3$—$CHOH$—$CH_2$—$OCH_3$ and $CH_3$—$CH(OCH_3)$—$CH_2OH$. When epichlorohydrin is manufactured, by-products are formed by reaction between the epichlorohydrin and water or methanol, and in particular 1-chloropropanediol and chloromethoxypropanols of formulae $ClCH_2$—$CHOH$—$CH_2$—$OCH_3$ and $Cl$—$CH_2$—$CH(OCH_3)$—$CH_2OH$. The formation of by-products reduces the selectivity of the process and consequently its yield.

The present invention is directed towards overcoming this drawback by providing a novel process of high selectivity, while at the same time maintaining high activity (or a high reaction rate).

To this end, the invention relates to a process for manufacturing oxirane by reacting an olefin with a peroxide compound in the presence of a catalyst and a solvent in at least two reactors arranged in series, each of which contains a portion of the catalyst, according to which a first portion of the olefin, the solvent and the peroxide compound are introduced into a first reactor, an epoxidation of the first portion of the olefin is carried out therein in order to form a first portion of the oxirane, a medium comprising the first portion of oxirane formed, the solvent, the unconverted olefin and, where appropriate, the unconsumed peroxide compound is removed from this reactor and introduced into a distillation column, the majority of the oxirane formed and of the unconverted olefin is collected at the top of the column, the medium depleted in oxirane and containing, where appropriate, the unconsumed peroxide compound is collected at the bottom of the column, the medium depleted in oxirane and another portion of the olefin and optionally another portion of the peroxide compound are introduced into a subsequent reactor, an epoxidation of the other portion of the olefin is carried out therein in order to form another portion of the oxirane, and the other portion of the oxirane thus formed is collected.

One of the essential characteristics of the present invention lies in the intermediate distillation carried out between the two epoxidation reactions. Specifically, this makes it possible to minimize the formation of by-products.

The distillation serves to remove the oxirane as quickly as possible as it is formed in the reaction medium in order to prevent it from being in contact with the other constituents of the reaction medium and to prevent by-products from being thus formed. This separation is carried out in a distillation column which is separate and distinct from the epoxidation reactor. Since the catalyst does not leave the epoxidation reactor, the distillation is thus carried out in the absence of the epoxidation catalyst in order to prevent contact between the oxirane formed and the epoxidation catalyst, since the latter promotes the formation of by-products.

The distillation makes it possible to separate the majority of the oxirane formed from the epoxidation reaction medium. This majority is generally greater than or equal to 80% of the amount of oxirane formed in the first reactor. It is usually greater than or equal to 90%. Usually, it is less than or equal to 99%. In particular, it is less than or equal to 95%.

The conditions under which the distillation is carried out depends on the nature of the oxirane (and in particular its boiling point), its concentration in the medium introduced into the distillation column, the nature of the other constituents of the medium (the unconverted olefin and the solvent), their boiling point and the desired distillation yield.

The distillation is generally carried out at a temperature of greater than or equal to 10° C., preferably greater than or equal to 35° C., values of greater than or equal to 45° C. being recommended. The temperature is usually less than or equal to 125° C., most commonly less than or equal to 100° C., values of less than or equal to 90° C. being preferred.

The distillation is commonly carried out at a pressure of greater than or equal to 0.1 bar, preferably greater than or equal to 0.5 bar, values of greater than or equal to 1 bar being the most common. The pressure is generally less than or equal to 10 bar, in particular less than or equal to 5 bar, values of less than or equal to 2 bar being most particularly recommended. In the present description, any reference to the distillation pressure corresponds to the absolute pressure measured at the top of the distillation column.

The distillation column which may be used in the process according to the invention is known per se. It is possible to use, for example, a column with conventional plates or a column with plates of "dual-flow" type or alternatively a column with loose or structured packing.

The number of theoretical plates in the distillation column is generally greater than or equal to 20 and more especially greater than or equal to 30. A number of less than or equal to 80 gives good results. A number of less than or equal to 60 is recommended.

The degree of molar reflux (which corresponds to the molar flow rate of liquid sent to the top of the column relative to the entire distillate—vapour plus liquid—taken from the top of the column) in the distillation column is usually greater than or equal to 0.5 and preferably greater than or equal to 0.8. This degree is commonly less than or equal to 5 and usually less than or equal to 2.5.

In the process according to the invention, a plant comprising at least two epoxidation reactors arranged in series and connected together is used. Each reactor is fed with olefin. The peroxide compound and the solvent are introduced into the first reactor. Fresh peroxide compound may also be introduced into one or more subsequent reactors. Each reactor contains a portion of the catalyst which does not leave this reactor. When the catalyst is present in the form of a fixed bed, it is generally not necessary to take precautions to keep the catalyst in the reactor. Alternatively, the catalyst may be present in the form of particles, at least some of which are in a form fluidized by a liquid stream or by mechanical stirring or by a gas. When a liquid stream is used, it is recommended to include a fall-out zone above the fluid bed in order to stop the catalyst particles which are in motion and/or to include a filter at the reactor outlet.

Needless to say, the plant may comprise more than two reactors connected in series. In this case, the first reactor of the series is fed with olefin, the peroxide compound, the solvent (and optionally a fraction of the medium obtained at the bottom of the distillation column corresponding to this reactor) and each subsequent reactor is fed with the olefin, the remainder of the medium obtained from the preceding reactor of the series and optionally fresh peroxide compound. Preferably, 3 reactors in series are used.

In the process according to the invention, reactors of identical size are preferably used. This makes it possible to interchange the function of the reactors when the deactivated catalyst in one reactor is replaced with fresh or regenerated catalyst without disrupting the functioning of the plant (so-called "carousel" functioning).

In a first embodiment of the process according to the invention, not only the first reactor of the series, but each subsequent reactor of the series is followed by a distillation column, which is referred to hereinbelow as "subsequent distillation". This subsequently distillation has the same function as the intermediate distillation carried out between the first and second epoxidation. The conditions of the subsequent distillations are similar to the conditions described above for the intermediate distillation. In this embodiment, the medium leaving each subsequent reactor and containing the other portion of the oxirane, the solvent, the unconverted olefin and, where appropriate, the unconsumed peroxide compound is introduced into a subsequent distillation column, the other portion of the oxirane and the unconverted olefin are collected at the top of the column, and the solvent and possibly the unconsumed peroxide compound are collected at the bottom of the column. In a continuous process, it may be advantageous to recycle the medium collected at the bottom of the last distillation column (and containing the solvent and possibly the unconsumed peroxide compound) into the first reactor. For example, when the process is carried out in two reactors in series, the medium collected at the bottom of the second distillation column may be recycled into the first reactor.

In a second embodiment of the process according to the invention, the mixture of oxirane and of unconverted olefin collected at the top of the distillation column (first and/or subsequent column) is introduced into a container in which the oxirane is separated from the unconverted olefin. This unconverted olefin may then be recycled into one of the reactors, preferably into the first reactor. The container may contain a condenser or an absorbent liquid or an absorbent solid or alternatively a permoselective membrane. Condensers are suitable for use.

A third embodiment of the process according to the invention consists in using the catalyst in the form of particles, at least a portion of which is in fluidized form, as disclosed in the Applicant's patent application filed on the same day as the present patent application and entitled "Process for manufacturing oxirane in the presence of a catalyst in the form of particles" (the content of which is incorporated by reference). In this case, it is recommended to include a filter through which the medium leaving the reactor (first and/or subsequent reactor) passes before being introduced into the distillation column (first and/or subsequent column). This embodiment makes it possible to obtain a homogeneous dispersion of the catalyst in the epoxidation medium, good heat exchange and thus easy control of the reaction temperature.

In a fourth embodiment of the process according to the invention, the medium entering the distillation column (first and/or subsequent column) is first subjected to a depressurization before being introduced into this distillation column. This embodiment is particularly suitable when the epoxidation is carried out under pressure or in the presence of a gaseous compound. This gaseous compound may be the olefin itself (for example propylene) or an inert gas which is introduced into the epoxidation reaction medium in order to allow the oxirane to be entrained and removed from the reactor, as disclosed in patent application WO 99/48883 by the Applicant.

In a fifth embodiment of the process according to the invention, all of the peroxide compound is introduced into the first reactor, as disclosed in the Applicant's patent application filed on the same day and entitled "Process for manufacturing oxirane using a peroxide compound" (the content of which is incorporated by reference). The subsequent reactor(s) are thus not fed with fresh peroxide compound, but only with the peroxide compound which is present in the medium obtained from the preceding reactor and which was not consumed in that previous reactor. In general, water is also introduced with the peroxide compound into the first reactor. The fact that no peroxide compound is added to the subsequent reactor(s) makes it possible to consume 100% of the total amount of peroxide compound used without, however, reducing the reaction rate, when compared with a process using the same total amount of peroxide compound but in which each reactor is fed with fresh peroxide compound.

A preferred embodiment of the process according to the invention is represented schematically in FIG. 1. In this preferred embodiment, the first reactor 1 contains a portion of the catalyst, preferably as a fluid bed 2. The reactor 1 is fed with a first portion of the olefin via pipe 3 and then via pipe 4, with peroxide compound via pipe 5 and then via pipe 4, and with solvent via pipe 4 from another part of the plant which is described later. In the first reactor, the first portion of the olefin reacts with the peroxide compound in the presence of the catalyst to form a first portion of the oxirane. The medium leaving the reactor 1 via pipe 6 contains the solvent, the first portion of the oxirane, the unconsumed peroxide compound and the unconverted olefin. This medium passes through a filter 7 and is conveyed via pipe 8 into the container 9 in which it is subjected to a depressurization. The medium is then transported via pipe 10 into a distillation column 11. A mixture of oxirane and of unconverted olefin is recovered at the top of this distillation column 11. This mixture is conveyed via pipe 12 into a condenser 13 which separates the oxirane from the unconverted olefin. The unconverted olefin is recycled into the reactor 1 via pipes 14, 3 and 4. The first portion of oxirane is collected as finished product via pipe 15. A medium containing the solvent, the peroxide compound not consumed in the reactor 1 and possibly a portion of the unconverted olefin is collected at the bottom of the distillation column 11. This medium, a portion of which may optionally be recycled into the reactor 1 via pipe 30, is transported via pipe 16 into a second reactor 17 containing another portion of the catalyst, preferably in the form of a fluid bed 18. The second reactor 17 is fed with a second portion of the olefin via pipe 19. In the second reactor 17, the second portion of the olefin reacts with the unconsumed peroxide compound from the first reactor in the presence of the catalyst 18 to form a second portion of the oxirane. The conditions in the second reactor 17 are preferably such that all of the peroxide compound from the first reactor is consumed. The medium leaving the reactor 17 via pipe 20 thus contains the solvent, the second portion of the oxirane and the unconverted olefin. This medium passes through a filter 21 and is conveyed via pipe 22 into the container 23 in which it is subjected to a depressurization. The medium is then transported via pipe 24 into a second distillation column 25. A mixture of the second portion of oxirane and of unconverted olefin is recovered at the top of this distillation column 25. This mixture is conveyed via pipe 26 into a condenser 27 which separates the oxirane from the unconverted olefin. The unconverted olefin is recycled into the reactor 1 via pipes 28, 14, 3 and 4. The second portion of oxirane is collected as finished product via pipe 29. The solvent, which is recycled via pipe 4 into the first reactor 1, and an aqueous effluent, which is evacuated via pipe 31, are collected at the bottom of the distillation column 25.

The catalyst used in the process according to the invention generally contains a zeolite as active element, and preferably a titanium zeolite. The term "titanium zeolite" is intended to denote a solid containing silica which has a microporous crystal structure of zeolite type and in which several silicon atoms are replaced with titanium atoms. The titanium zeolite advantageously has a crystal structure of ZSM-5, ZSM-11, ZSM-12, MCM-41 or ZSM-48 type. It may also have a crystal structure of beta zeolite type, preferably free of aluminium. Zeolites with an infrared absorption band at about 950–960 cm$^{-1}$ are suitable for use. Titanium zeolites of silicalite type are preferred. Those corresponding to the formula $xTiO_2(1-x)SiO_2$ in which x is from 0.0001 to 0.5 and preferably from 0.001 to 0.05 give high performance. Materials of this type, known under the name TS-1, have a microporous crystalline zeolite structure similar to that of zeolite ZSM-5.

The catalyst used in the process according to the invention is advantageously in the form of particles obtained by extrusion as disclosed in the Applicant's patent application WO 99/28029, or by a spray process as disclosed in the Applicant's patent application WO 99/24164. The content of these two patent applications is incorporated herein by reference.

The solvent used in the process according to the invention may be chosen from saturated, linear or branched aliphatic alcohols. The alcoholic solvent generally contains up to 10 carbon atoms, preferably from 1 to 6 carbon atoms. Examples which may be mentioned are methanol and ethanol. Methanol is preferred.

The amount of solvent used in the first reactor is generally at least 25% by weight of the liquid reaction medium present in the first reactor, in particular at least 40% by weight, for example at least 50% by weight. This amount usually does not exceed 99% by weight and in particular does not exceed 95% by weight.

The molar ratio between the amounts of olefin and of peroxide compound used in the process according to the invention is generally at least 0.1, in particular at least 0.2 and preferably at least 0.5. This molar ratio is usually not more than 100, in particular not more than 50 and preferably not more than 25.

The process according to the invention may be continuous or batchwise.

In the process according to the invention, when it is carried out continuously, the peroxide compound is generally used in the first reactor in an amount of at least 0.005 mol per hour and per gram of catalyst present in the first reactor, in particular of at least 0.01 mol. The amount of peroxide compound is usually less than or equal to 25 mol and in particular less than or equal to 10 mol. Preference is shown for an amount of peroxide compound of greater than or equal to 0.03 mol and less than or equal to 2.5 mol.

In the process according to the invention, the peroxide compound is advantageously used in the form of an aqueous solution. In general, the aqueous solution contains at least 2% by weight of peroxide compound, in particular at least 5% by weight. It usually contains not more than 90% by weight of peroxide compound, in particular 70% by weight.

The reaction temperature between the olefin and the peroxide compound may range from 10° C. to 125° C. In one advantageous variant as disclosed in patent application EP 99/08703 by the Applicant, it is greater than 35° C. to overcome the gradual deactivation of the catalyst. The temperature may be greater than or equal to 40° C. and preferably greater than or equal to 45° C. A temperature of greater than or equal to 50° C. is most particularly preferred. The reaction temperature is preferably less than 100° C.

In the process according to the invention, the reaction between the olefin and the peroxide compound may take place at atmospheric pressure. It may also be performed under pressure. This pressure generally does not exceed 40 bar. A pressure of 20 bar is suitable in practice.

The peroxide compounds which may be used in the process according to the invention are peroxide compounds containing one or more peroxide functions (—OOH) which may release active oxygen and which are capable of carrying out an epoxidation. Hydrogen peroxide and peroxide compounds which may produce hydrogen peroxide under the conditions of the epoxidation reaction are suitable for use. Hydrogen peroxide is preferred.

When hydrogen peroxide is used, it may be advantageous to use, in the process according to the invention, an aqueous hydrogen peroxide solution in crude form, i.e. in unpurified form. For example, a solution obtained by simple extraction with substantially pure water of the mixture derived from the oxidation of at least one alkylanthrahydroquinone (process known as "autoxidation AO process") without a subsequent washing and/or purification treatment may be used. These crude hydrogen peroxide solutions generally contain from 0.001 to 10 g/l of organic impurities expressed as TOC (Total Organic Carbon). They usually contain metal cations (such as alkali metals or alkaline-earth metals, for instance sodium) and anions (such as phosphates and nitrates) in contents of from 0.01 to 10 g/l.

In another variant of the process, a hydrogen peroxide solution produced by direct synthesis using oxygen and hydrogen in the presence of methanol may be used.

The oxirane which may be prepared by the process according to the invention is an organic compound comprising a group corresponding to the general formula:

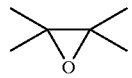

The oxirane generally contains from 2 to 10 carbon atoms, preferably from 3 to 6 carbon atoms. The oxiranes which may be prepared advantageously by the process according to the invention are 1,2-epoxypropane and 1,2-epoxy-3-chloropropane. The preferred oxirane is 1,2-epoxypropane.

The olefins which are suitable in the process according to the invention generally contain from 2 to 10 carbon atoms and preferably 3 to 6 carbon atoms. Propylene, butylene and allyl chloride are suitable for use. Propylene and allyl chloride are preferred, and most particularly propylene.

In the process according to the invention, it may prove to be advantageous to monitor the pH of the liquid phase. For example, it may be advantageous to maintain the pH of the liquid phase during the reaction between the olefin and the peroxide compound at a value of from 4.8 to 6.5, for example by adding a base (sodium hydroxide) to the epoxidation medium, as recommended in patent application WO 99/48882 by the Applicant (the content of which is incorporated by reference into the present patent application). This base may be introduced into a single reactor (for example the first reactor) or into several reactors. It is preferably introduced into each reactor.

The reaction between the olefin and the peroxide compound may be carried out in the presence of a salt such as sodium chloride, as disclosed in patent application WO EP 99/08703 by the Applicant (the content of which is incorporated by reference into the present patent application). This salt may be introduced into a single reactor (for example the first reactor) or into several reactors. It is preferably introduced into each reactor.

It may be advantageous to introduce the olefin in a form diluted in one or more alkanes. For example, a fluid containing the olefin and also at least 10% (in particular 20%, for example at least 30%) by volume of one or more alkanes may be introduced into the epoxidation reactors. For example, in the case of propylene, the latter may be mixed with at least 10% by volume of propane when the recycled unconverted propylene is introduced into the reactor. It may also be a source of propylene which is not completely freed of propane.

The examples that follow are intended to illustrate the present invention without, however, limiting its scope.

Examples 1 and 2 were calculated using the Aspen Plus® software from the company Aspen Technology Inc. using reaction kinetics parameters determined on the basis of the experimental results described and of the liquid-vapour equilibria available in the literature.

COMPARATIVE EXAMPLE 1

In this example, the synthesis of propylene oxide is performed in 2 reactors in series without intermediate separation of the propylene oxide formed in the first reactor.

326.5 kmol/h of hydrogen peroxide accompanied by 1 100 kmol/h of water are mixed with 1 500 kmol/h of methanol and 250 kmol/h of propylene under a pressure sufficient to dissolve all of the propylene at the reaction temperature. The reaction mixture is introduced continuously at 70° C. into a methodic reactor containing 600 kg of catalyst.

The reactor effluent is mixed with 200 kmol/h of propylene at a pressure sufficient to dissolve all of the propylene at the reaction temperature, and is introduced continuously at 70° C. into a second methodic reactor containing 600 kg of catalyst.

The effluent from the second reactor contains 2.3 kmol/h of unconverted hydrogen peroxide, 243.9 kmol/h of propylene oxide and 77.4 kmol/h of by-products (mainly methoxypropanol and propanediol); the yield of C3 is up to 74.7% for a degree of conversion of the hydrogen peroxide of 99.3%.

EXAMPLE 2

(In Accordance with the Invention)

In this example, the synthesis of propylene oxide is performed in 2 reactors in series with intermediate separation of the propylene oxide formed in the first reactor.

326.5 kmol/h of hydrogen peroxide accompanied by 1 100 kmol/h of water are mixed with 1 500 kmol/h of methanol and 250 kmol/h of propylene under a pressure sufficient to dissolve all of the propylene at the reaction temperature. The reaction mixture is introduced continuously at 70° C. into a methodic reactor containing 600 kg of catalyst.

The reactor effluent is conveyed to a rectification column containing 50 theoretical plates (including condenser and boiler); the feed is effected into the 10th theoretical plate (counting from the condenser); the column is run at 1.1 bar absolute (column head pressure); the column head temperature is maintained at 40° C. (partially vaporized distillate); the degree of molar reflux is set at 1; the flow rate of distillate is adjusted so as to recover at the top of the column 95% of the propylene oxide present in the column feed.

The mixture taken from the bottom of the column, which is depleted in propylene oxide, is mixed with 200 kmol/h of propylene at a pressure sufficient to dissolve all of the propylene at the reaction temperature, and is introduced continuously at 70° C. into a second methodic reactor containing 600 kg of catalyst.

The effluent from the second reactor contains 0.5 kmol/h of unconverted hydrogen peroxide, 85.9 kmol/h of propylene oxide and 68.5 kmol/h of by-products (mainly methoxypropanol and propanediol); the column distillate contains 168.8 kmol/h of propylene oxide; the yield of C3 is up to 78.0% for a degree of conversion of the hydrogen peroxide of 99.9%.

What is claimed is:

1. A process for manufacturing oxirane by reacting of an olefin with a peroxide compound in the presence of a catalyst and a solvent in at least two reactors arranged in series, each of which contains a portion of the catalyst, according to which a first portion of the olefin, the solvent and the peroxide compound are introduced into a first reactor, an epoxidation of the first portion of the olefin is carried out therein in order to form a first portion of the oxirane, a medium comprising the first portion of oxirane formed, the solvent, the unconverted olefin and, where appropriate, the unconsumed peroxide compound is removed from this reactor and introduced into a distillation column, the majority of the oxirane formed and of the unconverted olefin is collected at the top of the column, the medium depleted in oxirane and containing, where appropriate, the unconsumed peroxide compound is collected at the bottom of the column, the medium depleted in oxirane and another portion of the olefin and optionally another portion of the peroxide compound are introduced into a subsequent reactor, an epoxidation of the other portion of the olefin is carried out therein in order to form another portion of the oxirane, and the other portion of the oxirane thus formed is collected.

2. The process according to claim 1, in which the medium leaving the subsequent reactor and containing the other portion of the oxirane, the solvent, the unconverted olefin and possibly the unconsumed peroxide compound is introduced into a subsequent distillation column, the majority of the other portion of the oxirane and of the unconverted olefin are collected at the top of this column and the solvent and possibly the unconsumed peroxide compound are collected at the bottom of this column.

3. The process according to claim 2, in which the process is carried out in two reactors arranged in series and in which the medium collected at the bottom of the second distillation column is recycled into the first reactor.

4. The process according to claim 1, in which the mixture of oxirane and of unconverted olefin collected at the top of the distillation column (first and/or subsequent column) is introduced into a condenser in which the oxirane is separated from the unconverted olefin which is recycled into one of the reactors.

5. The process according to claim 1, in which all the reactors are of identical size.

6. The process according to claim 1, in which the catalyst is present in each reactor in the form of particles, at least a portion of which is in fluidized form.

7. The process according to claim 6, in which the medium leaving the reactor (first and/or subsequent reactor) passes through a filter before being introduced into the distillation column (first and/or subsequent column).

8. The process according to claim 1, in which the medium entering the distillation column (first and/or subsequent column) is first subjected to a depressurization before being introduced into this distillation column.

9. The process according to claim 1, in which all of the peroxide compound is introduced into the first reactor.

10. The process according to claim 1, in which the oxirane is propylene oxide or epichlorohydrin, the olefin is propylene or allyl chloride, the peroxide compound is hydrogen peroxide, the solvent is methanol and the catalyst contains TS-1.

11. The process according to claim 1, wherein no substantial amount of solvent is removed between reactors and immediate subsequent reactors.

12. The process according to claim 1, wherein three reactors arranged in series are used.

* * * * *